United States Patent
Reijnen

(10) Patent No.: US 12,409,025 B2
(45) Date of Patent: Sep. 9, 2025

(54) STENT GRAFT WITH SEALING ELEMENT

(71) Applicant: Bentley InnoMed GmbH, Hechingen (DE)

(72) Inventor: Michel M. P. J. Reijnen, Arnhem (NL)

(73) Assignee: Bentley Innomed GmBH, Hechingen (DE)

( * ) Notice: Subject to any disclaimer, the term of this patent is extended or adjusted under 35 U.S.C. 154(b) by 152 days.

(21) Appl. No.: 16/891,536

(22) Filed: Jun. 3, 2020

(65) Prior Publication Data
US 2020/0383770 A1     Dec. 10, 2020

(30) Foreign Application Priority Data
Jun. 4, 2019   (DE) .......................... 102019115021.3

(51) Int. Cl.
*A61F 2/07*   (2013.01)
*A61F 2/06*   (2013.01)

(52) U.S. Cl.
CPC .......... *A61F 2/07* (2013.01); *A61F 2002/061* (2013.01); *A61F 2002/072* (2013.01); *A61F 2210/0014* (2013.01); *A61F 2250/0023* (2013.01); *A61F 2250/0067* (2013.01); *A61F 2250/0069* (2013.01); *A61F 2250/0098* (2013.01); *A61F 2310/00017* (2013.01)

(58) Field of Classification Search
CPC ........ A61F 2002/077; A61F 2250/0069; A61F 2230/0065; A61F 2250/0098
See application file for complete search history.

(56) References Cited

U.S. PATENT DOCUMENTS

| | | | | |
|---|---|---|---|---|
| 2006/0259131 A1* | 11/2006 | Molaei | ...................... | A61F 2/07 623/1.44 |
| 2009/0319029 A1* | 12/2009 | Evans | ..................... | A61F 2/954 623/1.35 |
| 2011/0270378 A1* | 11/2011 | Bruszewski | .............. | A61F 2/07 623/1.35 |
| 2014/0277388 A1* | 9/2014 | Skemp | .................. | A61F 2/2418 623/1.26 |
| 2015/0122687 A1* | 5/2015 | Zeng | ..................... | A61F 2/0095 53/467 |
| 2017/0231749 A1* | 8/2017 | Perkins | ................. | A61F 2/0077 623/1.13 |
| 2020/0253710 A1* | 8/2020 | Ortega | ....................... | A61F 2/07 |
| 2020/0383769 A1* | 12/2020 | Xiao | ......................... | A61F 2/07 |

FOREIGN PATENT DOCUMENTS

EP   1839624 A1   10/2007
WO   WO-2018005969 A1 *   1/2018   ............... A61F 2/07

OTHER PUBLICATIONS

European Search Report dated Nov. 2, 2020, 7 pages.

\* cited by examiner

*Primary Examiner* — Leslie A Lopez
(74) *Attorney, Agent, or Firm* — Brooks Kushman P.C.

(57) ABSTRACT

The invention relates to a chimney stent graft with a tubular stent graft body (2) and at least one sealing element (3), wherein the sealing element (3) encloses the stent graft body (2) in a middle section and the sealing element (3) comprises a sponge- and/or tangle-like, elastic structure. The sealing element (3) provides for sealing of the gap forming between the chimney stent graft (1) and the vessel wall or further parallel stent grafts, resp., and thus prevents leakage.

11 Claims, 2 Drawing Sheets

STENT GRAFT WITH SEALING ELEMENT

Figure 1:
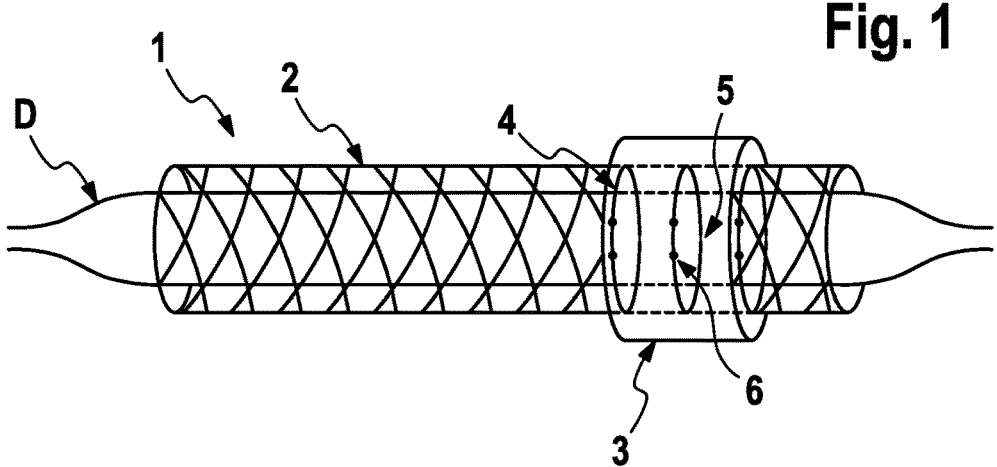

The invention relates to a stent graft with a sealing element for intravascular use, in particular with the chimney technique.

The treatment of abdominal aortic aneurysms is challenging. This in particular applies, when the treatment concerns a vessel section, which also includes visceral or renal arteries. In hospitals specialising in respective procedures, the mortality and complication rates may be comparatively low, also with open procedures, these positive results, however, are not transferable to the multitude of treatment centres.

Alternative minimally invasive interventions, with which an open procedure and the associated risk of wound infections or also the risk of general anaesthesia can be avoided, are known in the state of the art.

A possible form of the minimally invasive treatment of an (aortic) aneurysm provides bridging of the weakened vessel section, within which the aneurysm develops in the form of a sacculation of the weakened vessel wall. Here, a stent graft (a vascular prosthesis with a stent and a coating as impermeable to liquid as possible) is normally placed such that it bridges the weakened vessel section and thus prevents a possible rupture of the aneurysm.

A disadvantage of this technique is that, with the stent graft, frequently not only the weakened vessel section, i.e. the aneurysm itself, but also further side branches branching off from the affected vessel are covered and thus may be cut off from blood supply. This may result in an insufficient supply of organs and tissues depending on these vessels.

In order to prevent these known complications, in particular two implantation techniques are currently established. On the one hand, the stent graft to be implanted can be especially adapted to the vascular anatomy of the patient. Such individualised stent grafts are either based on the modular principle or are newly manufactured in their entirety. The disadvantage of such individualised systems is that they are rather expensive to purchase, above all when these are complete customisations. Furthermore, such systems are not directly available in case of an emergency, but must be adapted or manufactured, resp., first, even in case of modular systems. With complete customisations, this may take days to weeks.

Another known implantation technique provides respectively reconnecting covered side branches to the blood supply of the main branch with their own stent grafts. One of these techniques, the so-called "chimney technique", has particularly proven itself in recent times.

With the chimney technique, the connection of the side branches, which were covered by the stent graft placed in the main branch, with the blood stream is re-established by inserting further stent grafts, adapted to the diameter of the respective side branch, in parallel to the main branch stent graft. In that, the normally considerably smaller side branch stent graft extends from the beginning of the main branch stent graft, which it protrudes by a few millimetres, right into the side branch. The "protruding" of the main branch stent graft by the side branch stent graft characteristic for this technique resembles a chimney.

The chimney technique offers many advantages compared to other intervention techniques. Thus, for example, common stent grafts can be used for the entire intervention and no models adapted to the special vascular anatomy have to be manufactured. This makes this technique not only available any time—also in cases of emergency—but additionally comparatively cost-effective.

A disadvantage of the chimney technique with conventional stent grafts, however, is that, above all, interstices, cracks or gaps and consequently leakages may inevitably occur between the stent grafts and the vessel wall due to the round shapes of the various stent grafts resting against each other, when blood passes through these interstices. These leaks designated as type 1 a endoleakages may have a negative impact on the longevity of such an arrangement of stent grafts.

A further disadvantage of the chimney technique with conventional stent grafts consists in the competing radial forces and the constraints of expansion of the stent grafts running in parallel. Thus, there is a potential risk that the diameters of the stent grafts running in parallel mutually restrict each other, which again may result in a hazardous insufficient supply of the respectively connected organs and tissues. This risk particularly exists in the area of the branch-off into the side branch.

Especially upon using conventional stent grafts, this risk is particularly high, since, tendentially, their diameters have to be chosen rather larger in order to minimise the risk of leakages. Exactly this, however, simultaneously results in a clash of higher radial forces and thus in a higher risk of the diameter reductions described.

Accordingly, generally two interests conflict with one another upon selecting a suitable stent graft for the chimney technique: On the one hand, the stent graft is to be as flexible as possible, in order to achieve good fitting accuracy and thus sealing. On the other hand, however, the radial force must also be high enough to resist the pressure of the actual stent graft in the main branch. A higher radial force, however, always also results in lower flexibility and vice versa.

In order to overcome these clashing interests of the user and the conflicting requirements to the stent graft, various devices were suggested in the state of the art.

For avoiding or minimising, resp., leakages upon placing stent grafts, for example, within the scope of the chimney technique, WO 2017/114302 A1 and WO 2017/114305 A1 describe a device, in which two stent grafts are combined such that a first stent graft is at least partially enclosed by a second stent graft in a collar-like fashion. The second stent graft is fixed to the outer side of the first stent graft with at least one of its ends. A comparable solution had already been suggested earlier by WO 2004/000167 A1.

A disadvantage of these known stent grafts upon using them in the chimney technique is, among other things, that a stent-in-stent-like situation is created, which results in stiffening of the vessel at this point. This, however, should be avoided in any case. The known devices also do not create sufficient sealing right into the narrowest areas between the stents resting against one another, so that, despite using these special stent grafts, leakages may still occur.

In addition, with the arrangement of two stents overlapping one another in a collar-like fashion, undesired and disadvantageous flow patterns may occur in the vessel, which, in the long run, have a negative impact on the patency rate of the vessel or the stent graft, i.e. result in vasoconstrictions or subsequently even in blockages by the unwanted formation of thrombi.

Not least, with the stent-in-stent arrangement, a stent graft of the known design always also results in a larger profile, i.e. in a larger diameter, which may complicate its use in smaller vessels or even make it impossible.

Therefore, it is an object of the invention to provide a stent graft, hereinafter designated as "chimney stent graft" for reasons of distinctness, which overcomes the disadvantages stated and is in particular suitable for use with the chimney technique.

This object is solved by an invention with the features of claim 1. Advantageous embodiments respectively are the subject matter of the dependent claims. It shall be pointed out that the features individually listed in the claims may also be combined with one another in any desired and technologically reasonable manner and thus demonstrate further embodiments of the invention.

A chimney stent graft according to the invention comprises a stent graft body and at least one sealing element.

If a "stent graft body" as part of the chimney stent graft according to the invention is discussed, in order to create a distinction from known stent grafts, this shall mean the stent graft portion of the chimney stent graft according to the invention without sealing elements.

For reasons of better comprehensibility, in the following, always only "one" or "the" sealing element is to be discussed, even though according to the invention more than one sealing element may be provided.

In its setup, the stent graft body as such substantially corresponds to known stent grafts (vascular prostheses) with an expandable stent (the metal frame) and a sheath fixed to the stent (the "graft"). Normally the sheath comprises a polymer sheath substantially impermeable to liquid, which at least partially encloses the stent.

The stent graft body may be balloon-expandable or self-expandable, wherein balloon-expandable stent grafts are to be preferred due to their higher radial force. The sheath may comprise the materials typical for stent grafts, like various polymers and in particular PTFE. The sheath may also have a multi-layered structure and comprise additional coatings, which, for example, have antithrombogenic, anti-restenotic or antibiotic properties, to name but a few. Here, the skilled person is familiar with a multitude of materials and active substances, from which he/she may select the materials and active substances suitable for the respective purpose.

The sealing element of the chimney stent graft according to the invention is provided in the middle section of the stent graft body. According to the invention, the middle section is defined as the section of the stent graft body, which respectively maintains a distance of 1 to 15 mm, and preferably of 5 to 10 mm, to the distal and proximal ends of the stent graft body. If several sealing elements are provided, then preferably in particular two sealing elements are provided in the middle section of the stent body.

Preferably, the sealing element is substantially formed in the shape of a hollow cylinder or ring-shaped, resp. According to the respective requirements, however, sealing elements of other shapes may also be provided, for example conically tapering, dumbbell-shaped, corrugated, round or entirely amorphous sealing elements. Such shapes may be respectively advantageous in variously formed vascular anatomies. An amorphous shape, for example, may be advantageous upon using the chimney stent graft in irregularly shaped vessels. Here, the skilled person will choose that shape, without becoming inventively active, that promises the best possible sealing for the application.

Preferably, the ends of the walls of the sealing element are designed almost angularly, wherein embodiments with rounded or even only partially rounded ends of the walls are also conceivable. Here, too, the skilled person decides in favour of that shape, which promises the best possible sealing for the respective intended use.

The inner diameter of the freely expanded sealing element substantially corresponds to the outer diameter of the freely expanded stent graft body. Just like the stent graft body, the sealing element may also be compressed to a smaller diameter. The inner diameter of the compressed sealing element then substantially corresponds to the outer diameter of the compressed stent graft body.

If the term "freely expanded" is used, then, according to the invention, this shall mean a state, in which the respective element, i.e. the chimney stent graft in its entirety, the stent graft body alone or the sealing element alone, has reached the respectively maximally provided expanded state without external constraints at the temperature intended for the application. For a balloon-expandable element, for example, this is the expansion of the element using balloon expansion to the nominal diameter provided, and for a self-expanding element, it is the expansion outside a delivery element without external constraints, respectively at a temperature, which corresponds to the average human body temperature in the vessel. Accordingly, for reasons of comprehensibility and objectivity, possible dimensional specifications refer to the freely expanded state, unless stated otherwise.

The maximum outer diameter of the freely expanded sealing element is between 1 and 10 mm, preferably between 2 and 8 mm, and in particular between 3 and 6 mm larger than the inner diameter of the freely expanded sealing element.

Preferably, the sealing element is provided concentrically around the stent graft body, however, embodiments are also conceivable, in which the sealing element is eccentrically arranged around the stent graft body. Such an eccentric arrangement of the sealing element may, for example, be advantageous upon use of the chimney stent graft in irregularly shaped vessels. A concentric arrangement of the sealing element, on the other hand, should be able to cover the largest range of standard interventions, in which a common vascular morphology is encountered.

Upon attachment of the sealing element, whether this is undertaken eccentrically or concentrically, it is important that sufficient adaptation to the given surroundings is possible.

The sealing element is connected with the stent graft body and adapts to the circumference of the stent graft body in the compressed state just as in the expanded state. The sealing element may be temporarily and/or permanently connected with the stent graft body.

According to the invention, a temporary connection of stent graft body and sealing element shall mean such a connection, which is provided in a detachable fashion during or after, resp., placement and expansion of the chimney stent graft. Accordingly, following implantation, the relative arrangement of stent graft body and sealing element to one another is permanently maintained, above all due to the pressures acting upon one another between stent graft body and sealing element, on the one hand, as well as (main branch) stent graft and vessel wall, on the other hand.

Examples for such a temporary connection are, for example, the sewing together with bioresorbable threads or the gluing together with bioresorbable adhesives of sealing element and at least parts of the stent graft body.

Also conceivable are temporary connections, in which the sealing element is arranged at the stent graft body by means of particularly ring-shaped holding elements, wherein the ring-shaped holding elements preferably have predetermined breaking points, which tear upon expansion of the chimney stent graft and thus enable an expansion of the chimney stent graft. Here, instead of ring-shaped holding elements, for example, a tubular film or threads could also be provided, which tear along a perforated seam upon expansion. The skilled person is familiar with further techniques, from which he/she selects a suitable one.

According to the invention, a permanent connection of stent graft body and sealing element, on the other hand, shall mean such a connection, which remains intact even after placement and expansion of the chimney stent graft. In that, the relative arrangement of stent graft body and sealing element to one another is also or above all maintained by the permanent connection of stent graft body and sealing element.

Examples for such a permanent connection are, for example, the sewing, gluing or welding together, also ultrasonic welding, of sealing element and at least parts of the stent graft body. Here, the skilled person selects a suitable technique.

Combinations of permanent and temporary connections are conceivable. Thus, the sealing element, for example, can be permanently connected with the stent graft body and comprise additional ring-shaped holding elements with predetermined breaking points, which encircle the sealing element and thus fix its compressed state. Based on these examples, the skilled person will easily be able to select further suitable embodiments, without having to be become inventively active in that.

In order to facilitate the placement of the chimney stent graft, additional radiopaque markers may be provided in the area of the sealing element in addition to the known radiopaque markers at the ends of the stent graft body. These additional markers may be provided, for example, at respective positions of the stent graft body, at the sealing element or, if applicable, at existing holding elements. The additional markers facilitate the placement of the chimney stent graft according to the invention by indicating those areas to the treating physician relevant for the desired sealing.

Materials for respective radiopaque markers are known to the skilled person.

The sealing element serves the sealing of passages between the stent graft body, on the one hand, and the vessel wall as well as the other stent grafts, as for example the (main branch) stent graft, on the other hand. For that, the sealing element comprises a biocompatible material, which may flexibly adapt to the outer surroundings or fit into the outer surroundings, resp.

It is particularly important that the material for the sealing element is highly compressible, on the one hand, but also, even after a longer period, re-expands to the original non-compressed state, on the other hand. Therefore, the state of compression should be completely reversible, if possible.

In that, it is essential for the invention that the sealing element has a sponge- and/or tangle-like and simultaneously elastic structure. According to the invention, such a structure shall mean structures, which have an own volume and compactness and thus may prevent a passage of liquids to the largest possible extent, however, simultaneously are sufficiently compressible to be placed in a catheter. A sponge- and/or tangle-like structure in terms of this patent may thus be a porous as well as a highly branched or ramified, resp., structure. A suitable tangle may, for example, be formed of only one or few filaments, however, tangles of a multitude of filaments up to non-woven fabric-like structures are also conceivable.

Suitable materials for the sealing element comprise, among others, in particular shape-memory materials, as, for example, shape-memory polymers (SMP) or shape-memory alloys (SMA) or spring steels. Here, known materials are, for example, nitinol and others.

Further suitable materials for the sealing element also comprise other flexible materials, in particular elastic polymers (elastomers), which after compression may return into an expanded state. These include most different polymers, as, for example, various polyurethane compounds.

Accordingly, a sponge-like structure of the sealing element according to the invention can be achieved by most different materials and material combinations. Possible structures comprise, for example, braided and non-braided materials, non-woven fabrics or also materials or material combinations arranged in a multi-layered fashion, or combinations therefrom.

Beside the certain shape or the use of certain structures, which promote the formation of thrombi, the sealing element preferably also has additional thrombogenic properties. The sealing element may respectively be manufactured from thrombogenic materials, as, for example, various polyamides, like PET or nylon, to name but a few. The sealing element may also be coated with a thrombogenic agent. Here, the skilled person has a multitude of known thrombogenic coating agents at his/her disposal. The advantage of using structures promoting thrombi as well as thrombogenic materials or coatings is that an additional sealing of the sealing element is achieved by a thrombus forming at the thrombogenic material. The sealing element is respectively reinforced in its perfect-fit state and its sealing by the formation of thrombi.

A sealing element with such a structure according to the invention has substantial advantages compared to the umbrella-shaped sealing elements known from the state of the art.

Thus, with the sealing element essential to the function, a tighter seal than with the known umbrella-like systems is possible, because it can expand considerably tighter also into the finest of gaps. With the special sealing element, the chimney stent graft according to the invention also withstands the blood stream acting on the seal better. An umbrella-like construction always involves the risk of collapsing with too high pressures and thus enabling a passage. Only with the particularly tight and stable seal provided by the compactness of the sealing element according to the invention, leakage is reliably prevented also in the long term.

The chimney stent graft according to the invention may also be designed and manufactured with a considerably higher radial force of the stent graft body, since the sealing, which actually requires an increased flexibility of the stent graft, is now achieved with the flexible separate sealing element.

These characteristics make the use of the chimney stent graft according to the invention also interesting, for example, in connection with endovascular aortic repairs (EVAR), since it is exactly these characteristics of good sealing in connection with a high radial force that are required here.

Moreover, with the sealing element according to the invention, compared to the known devices, a stent-in-stent-like situation is also avoided, which results in stiffening of the vessel at this point, which should be avoided in any case.

Not least, the chimney stent graft according to the invention can be manufactured with a smaller profile and thus also be used in smaller vessels.

Although the present invention has been continuously designated as "chimney stent graft", this designation has only been chosen for reasons of simplicity and only as an example for a possible application of the device according to the invention. Thus, the designation shall in no way be understood as limiting to a respective application with the chimney technique. The skilled person will find further possible applications of a stent graft body with sealing element according to the invention in daily clinical practice without any problem, for which it is just as suitable as within the scope of the chimney technique.

In the following, the invention as well as the technical environment will be explained in more detail based on the figures. It shall be pointed out that the figures show a particularly preferred embodiment of the invention. The invention, however, is not restricted to the embodiment shown. In particular, the invention, as far as technically reasonable, comprises any combinations of the technical features listed in the claims or described as relevant to the invention in the description.

THE FIGURES SHOW

FIG. 1 A first embodiment of the chimney stent graft according to the invention

Figure 2:
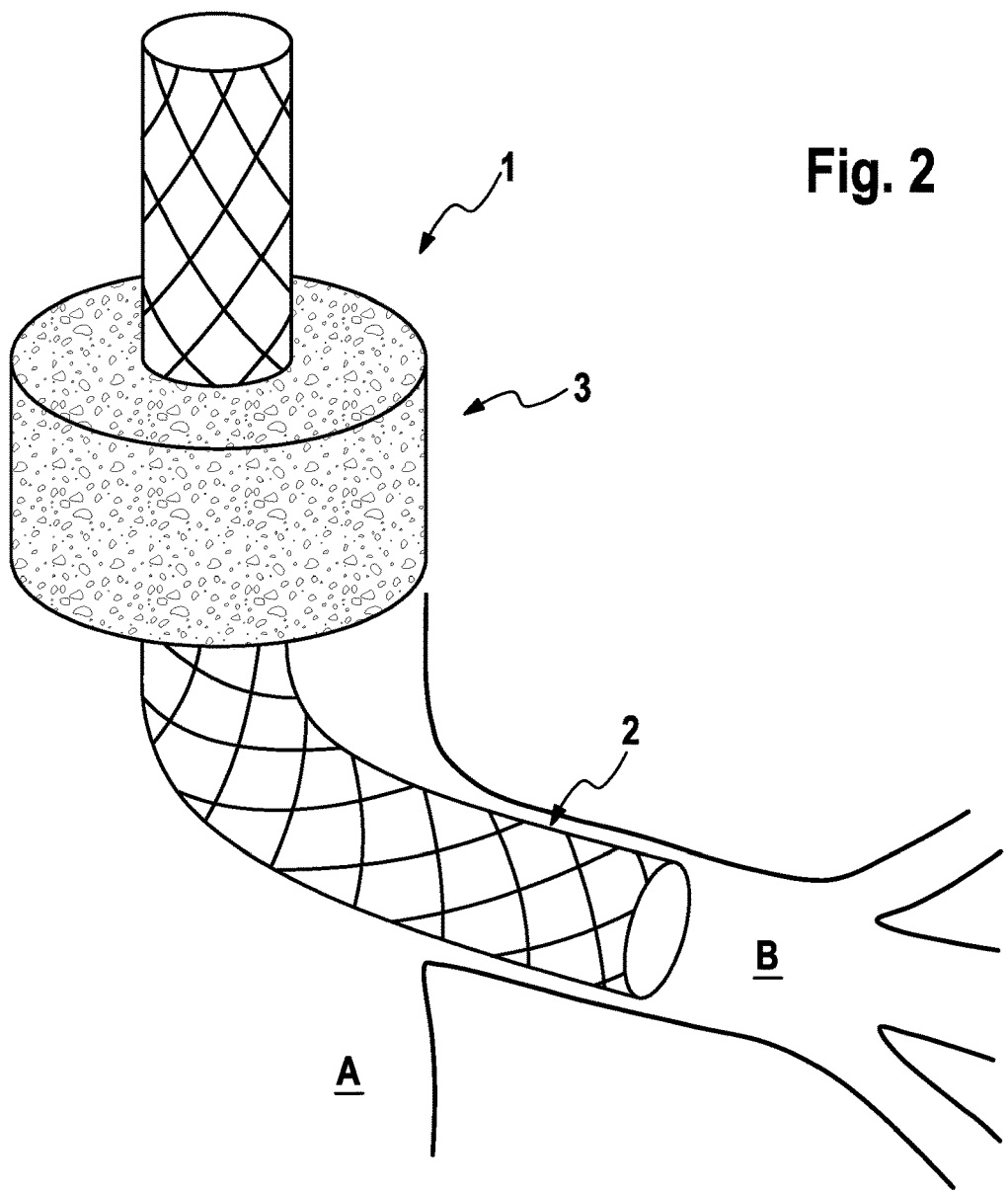

FIG. 2 Detailed views of the sealing element

Figure 3:
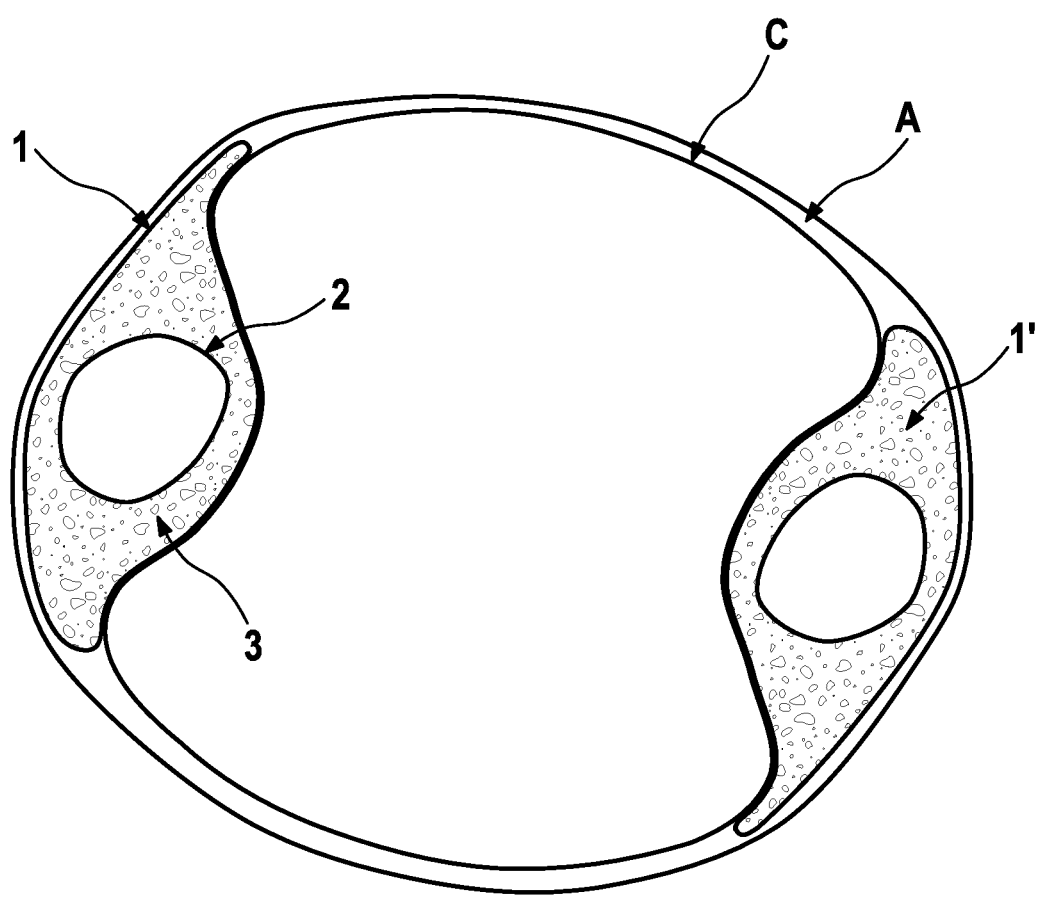

FIG. 3 A cross-section through a blood vessel with a main branch stent graft and two chimney stent grafts according to the invention FIG. 1 shows a first embodiment of a chimney stent graft 1 according to the invention. The chimney stent graft 1 is crimped onto a balloon catheter D and comprises a stent graft body 2 and a sealing element 3.

The sealing element 3 comprises an elastic, sponge-like material, which, as indicated, has a porous or highly branched or ramified, resp., or fibrous structure. In any case, the sealing element 3 is solid and voluminous in the sense that it, above all, does not consist of only a thin membrane, possibly held by clamping elements.

The sealing element 3 is connected with the stent graft body 2 by ring-shaped holding elements 4. The holding elements 4 comprise predetermined breaking points 5, which break upon expansion of the stent graft body 2. Additional radiopaque markers 6 may be provided in the area of the sealing element 3, which facilitate placement of the chimney stent graft 1 by indicating the position of the sealing element 3. These markers 6 may, for example, be provided at the stent graft body 2, the sealing element 3 or at least one of the holding elements 5.

FIG. 2 shows an example of a longitudinal cut through a blood vessel A (the main branch), in which a chimney stent graft 1 according to the invention has been placed in the main branch A. It can be seen that the chimney stent graft 1 distally protrudes into the side branch B and thus connects it to the blood supply via the main branch A.

FIG. 3 shows a cross-section through a blood vessel A (the main branch) at a point, where one main branch stent graft C and two chimney stent grafts 1, 1' according to the invention have been placed in parallel to one another. At this point, the stent graft body 2 is surrounded by the sealing element 3. The sealing element 3 completely fills the gap forming between vessel wall, stent graft body 2 and main branch stent graft C, and thus prevents leakage.

LIST OF REFERENCE SIGNS 1, 1' Chimney stent graft
2 Stent graft body
3 Sealing element
4 Holding element
5 Predetermined breaking point
6 Marker
A Main branch
B Side branch
C Main branch stent graft
D Balloon catheter

The invention claimed is:

1. A chimney stent graft, comprising a tubular stent graft body (2) and at least one sealing element (3) for sealing passages between the stent graft body and a vessel wall and a main branch stent graft, the stent graft body (2) comprising a stent and a sheath fixed to the stent, and wherein the sealing element (3) encloses the stent graft body (2) in a middle section, characterised in that the sealing element (3) consists of a material capable of forming a spongy elastic structure, the material being reversibly compressible and in that the sealing element is temporarily connected to the stent graft body prior to expansion of the chimney stent graft and is disconnected upon expansion, and wherein the sealing element (3) further comprises a thrombogenic coating and/or having thrombogenic properties.

2. The chimney stent graft according to claim 1, characterised in that the sealing element (3) is formed in a shape of a hollow cylinder or ring-shaped.

3. The chimney stent graft according to claim 1 characterised in that the spongy structure of the sealing element (3) comprises at least one material selected from the group consisting of shape-memory polymers (SMP), shape-memory alloys (SMA), spring steels, and elastomers.

4. The chimney stent graft according to claim 3, characterised in that the at least one material giving rise to the spongy structure of the sealing element are arranged in a multi-layered fashion.

5. The chimney stent graft according to claim 4, characterised in that an outer diameter of the sealing element (3) in an uncompressed state is by 1 to 10 mm larger than an outer diameter of the stent graft body (2).

6. The chimney stent graft according to claim 1, characterised in that an inner diameter of the sealing element (3) corresponds to an outer diameter of the stent graft body (2).

7. The chimney stent graft according to claim 1, characterised in that the stent of the stent graft body (2) comprises a self-expanding or balloon-expandable stent.

8. The chimney stent graft according to claim 1, characterised in that the sealing element (3) is fixed to the stent graft body (2).

9. The chimney stent graft according to claim 1, characterised in that radiopaque markers are provided within or adjacent the sealing element (3).

10. The chimney stent graft according to claim 1, characterised in that an outer diameter of the sealing element (3) in the uncompressed state is by 2 to 6 mm larger than an outer diameter of the stent graft body (2).

11. The chimney stent graft according to claim 1, characterised in that an outer diameter of the sealing element (3) in the uncompressed state is by 3 to 5 mm larger than an outer diameter of the stent graft body (2).

* * * * *